US012673885B2

(12) United States Patent
Wang et al.

(10) Patent No.: US 12,673,885 B2
(45) Date of Patent: Jul. 7, 2026

(54) METHOD OF PREPARING FeMnCeO$_x$ BIOMATERIAL AND METHOD OF TREATING ANTIBIOTIC WASTEWATER

(71) Applicant: Qingdao University of Technology, Qingdao (CN)

(72) Inventors: Huawei Wang, Qingdao (CN); Yanan Wang, Qingdao (CN); Yingjie Sun, Qingdao (CN); Jing Song, Qingdao (CN); Mengfan Liu, Qingdao (CN); Yanru Zhang, Qingdao (CN); Xutong Jiang, Qingdao (CN)

(73) Assignee: Qingdao University of Technology, Qingdao (CN)

( * ) Notice: Subject to any disclaimer, the term of this patent is extended or adjusted under 35 U.S.C. 154(b) by 480 days.

(21) Appl. No.: 18/499,139

(22) Filed: Oct. 31, 2023

(65) Prior Publication Data

US 2024/0059593 A1     Feb. 22, 2024

(30) Foreign Application Priority Data

Jun. 26, 2023     (CN) .......................... 202310759606.2

(51) Int. Cl.
| | |
|---|---|
| *B01J 23/00* | (2006.01) |
| *B01J 37/32* | (2006.01) |
| *B01J 37/36* | (2006.01) |
| *C02F 1/66* | (2023.01) |
| *C02F 1/72* | (2023.01) |
| *C12N 1/205* | (2026.01) |
| *C12P 3/00* | (2006.01) |
| *C12R 1/38* | (2006.01) |
| *C02F 101/38* | (2006.01) |

(52) U.S. Cl.
CPC .............. *C02F 1/725* (2013.01); *B01J 23/002* (2013.01); *B01J 37/32* (2013.01); *B01J 37/36* (2013.01); *C02F 1/66* (2013.01); *C12N 1/205* (2021.05); *C12P 3/00* (2013.01); *B01J 2523/3712* (2013.01); *B01J 2523/72* (2013.01); *B01J 2523/842* (2013.01); *C02F 2101/38* (2013.01); *C02F 2305/026* (2013.01); *C12R 2001/38* (2021.05)

(58) Field of Classification Search
CPC .............. B01J 37/36; B01J 2523/3712; C12R 2001/38
See application file for complete search history.

(56) References Cited

FOREIGN PATENT DOCUMENTS

| | | |
|---|---|---|
| CN | 113862307 A | 12/2021 |
| CN | 114272905 A | 4/2022 |

OTHER PUBLICATIONS

Zhang et al—CN 113862307 A FIT Translation—Dec. 31, 2021 (Year: 2021).*
Hou et al—CN 114272905 A FIT translation—Apr. 5, 2022 (Year: 2022).*

* cited by examiner

*Primary Examiner* — Bradley R Spies

(57) ABSTRACT

A method of preparing a FeMnCeO$_x$ biomaterial is provided, including the following steps. A *Pseudomonas* sp. strain KW-2 is obtained. A culture medium with a pH of 6.5-7.8 is prepared, which includes 0.1 g/L K$_2$HPO$_4$, 0.2 g/L MnSO$_4$·7H$_2$O, 0.2 g/L NaNO$_3$, 0.1 g/L CaCl$_2$), 0.1 g/L NH$_4$Cl, 0.1 g/L (NH$_4$)$_2$CO$_3$, 35 g/L NaCl and 150 mg/L ferric ammonium citrate. The culture medium is autoclaved, inoculated with the KW-2 strain, cultured for 1-3 days, added with a cerium nitrate solution, cultured for 3-7 days and centrifuged at 4,000-8,000 rpm for 10-20 min to collect a precipitate. The precipitate is rinsed 5-8 times with deionized water and 0.01 mol/L phosphate buffered saline (PBS) and freeze-dried at −60° C. to obtain the FeMnCeO$_x$ biomaterial. A method for treating antibiotic wastewater using the FeMnCeO$_x$ biomaterial is also provided.

10 Claims, 6 Drawing Sheets

METHOD OF PREPARING FeMnCeO$_x$ BIOMATERIAL AND METHOD OF TREATING ANTIBIOTIC WASTEWATER

CROSS-REFERENCE TO RELATED APPLICATIONS

This application claims the benefit of priority from Chinese Patent Application No. 202310759606.2, filed on Jun. 26, 2023. The content of the aforementioned application, including any intervening amendments thereto, is incorporated herein by reference in its entirety.

TECHNICAL FIELD

This application relates to water environment remediation and treatment, and more particularly to a method of preparing a FeMnCeO$_x$ biomaterial and a method of treating antibiotic wastewater.

BACKGROUND

Antibiotics are a class of compounds with bacteriostatic or bactericidal effects and are widely used in the medical field. At present, there are thousands of synthetic antibiotics, mainly including macrolides, β-lactams, and aminoglycosides. Antibiotics are widely produced and used in China. According to statistics, in 2020, the total use of veterinary antimicrobials in China reaches 33,000 tons, among which the tetracycline antibiotics are the most used and account for 30.52% of the total use. The parent compounds or metabolites of the antibiotic may be very stable. Therefore, the antibiotic cannot be fully absorbed and utilized and thus enters the water environment. This will not only result in the enhancement of resistance of sensitive bacteria, leading to the widespread of antibiotic resistance genes, but also endanger human health. Antibiotic pollution is widespread in the water environment. The survey revealed that antibiotics, such as tetracycline and sulfadiazine, are frequently detected in sewage plant effluent, river water, and water sources, and some antibiotic concentrations even reach the level of mg/L.

Currently, antibiotic wastewater is treated by biological, physical, and chemical methods. Physical methods mainly include adsorption and membrane separation, which are generally used in combination with other methods. Chemical methods include coagulation, flocculation, and precipitation. However, these chemical methods generally have slow treatment efficiency, low removal rate, and tendency to cause secondary pollution, and therefore are less used for treating antibiotic wastewater. Antibiotic wastewater contains bio-inhibitory substances and bacteria resistant to drugs, so biological treatment methods are less effective. Consequently, most antibiotic wastewater is hardly biodegradable wastewater rich in biotoxicity. Advanced oxidation technology with free hydroxyl groups as the primary oxidant has good effects on the treatment of hardly biodegradable wastewater, including the Fenton-like reagent method, ozone catalytic oxidation, electrochemical advanced oxidation, and photocatalytic oxidation, which has the advantages of wide application range, high oxidative property, fast reaction rate, and no pollution or less pollution.

The advanced oxidation method based on permonosulfate (PMS) is characterized by low cost, simple operation, and easy control, and thus has been widely used to treat refractory pollutants. PMS is an asymmetric oxidant that can be activated to produce hydroxyl radicals and sulfate radicals.

Usually, PMS can be activated by using transition metals (homogeneous and inhomogeneous), ultraviolet, ultrasonic, conduction electrons, and carbon catalysts. Generally, the sulfate radicals can be generated by activating PMS with a non-homogeneous catalyst system having transition metal oxides. However, the synthetic preparation process of conventional metal oxides is complicated and usually requires dangerous and expensive compounds as reducing or stabilizing agents and extreme conditions (such as high temperatures and high pressures), limiting their application.

In view of the drawbacks of traditional chemical methods, biosynthesis can be used as one of the important alternatives for metal oxide catalysts. Many microorganisms, such as bacteria, fungi, and algae, are capable of inducing the oxidation of transition metals, such as Fe (II) and Mn (II), which can usually be carried out under ambient conditions, such as neutral, ambient temperature, and atmospheric pressure. Bio-manganese oxidation of ferromanganese oxidizing bacteria induces ferromanganese oxides to achieve heavy metal fixation and organic pollutant degradation. It has been shown that metal-doped bio-ferromanganese oxides can change the mineral surface properties and further promote electron transfer between metals, lattice oxygen, structural defects, and PMS molecules while increasing the structural defects in the bulk phase, thus enhancing the catalytic activity and pollutant degradation performance. The rare earth element cerium (Ce) is widely used as a catalyst for the activation of PMS, a Fenton-like system, and ozone. However, the study on the efficacy of Ce-doped bio-ferromanganese oxides for antibiotic degradation is relatively few.

SUMMARY

An objective of the present disclosure is to provide a method of preparing a FeMnCeO$_x$ biomaterial and a method of treating antibiotic wastewater, so as to solve the technical problems in the prior art that the existing chemical methods involve complicated preparation of catalytic materials, harsh conditions (strong alkali) and high costs.

In a first aspect, this application provides a method of preparing a FeMnCeO$_x$ biomaterial, comprising:

obtaining a KW-2 strain, wherein the KW-2 strain is *Pseudomonas* sp. strain KW-2 with a national center for biotechnology information (NCBI) accession number of OM763989;

preparing a culture medium, wherein the culture medium comprises 0.1 g/L K$_2$HPO$_4$, 0.2 g/L MnSO$_4$·7H$_2$O, 0.2 g/L NaNO$_3$, 0.1 g/L CaCl$_2$), 0.1 g/L NH$_4$Cl, 0.1 g/L (NH$_4$)$_2$CO$_3$, 35 g/L NaCl and 150 mg/L ferric ammonium citrate; and a pH of the culture medium is 6.5-7.8;

autoclaving the culture medium; inoculating the KW-2 strain into the culture medium followed by a first culture for 1-3 days, wherein the KW-2 strain is 2-10% by volume of the culture medium; and adding a cerium nitrate solution into the culture medium followed by a second culture for 3-7 days and centrifugation at 4,000-8,000 rpm for 10-20 min to collect a precipitate; and rinsing the first precipitate 5-8 times with deionized water and a 0.01 mol/L phosphate buffered saline (PBS) followed by freeze-drying at −60° C. to obtain the FeMnCeO$_x$ biomaterial.

In an embodiment, during preparation of the culture medium, a MnSO$_4$·7H$_2$O solution is added, and a concentration of divalent manganese ions in the MnSO$_4$·7H$_2$O solution is 20-140 mg/L.

In an embodiment, during preparation of the culture medium, a ferric ammonium citrate solution is added, and a concentration of ferric ions in the ferric ammonium citrate solution is 50-180 mg/L.

In an embodiment, a concentration of cerium ions in the cerium nitrate solution is 5-50 mg/L.

In an embodiment, the culture medium is autoclaved at 121° C. for 15 min; and the first culture is performed at a rotation speed of 130 rpm and 25° C.

In a second aspect, this application provides a method for a treating antibiotic wastewater, comprising:

preparing a FeMnCeO$_x$ biomaterial using the aforementioned method; and adding the FeMnCeO$_x$ biomaterial and a permonosulphate (PMS) into the antibiotic wastewater; and adjusting a pH of the antibiotic wastewater followed by uniform mixing for degradation treatment of the antibiotic wastewater.

In an embodiment, a dosage of the FeMnCeO$_x$ biomaterial is 10-200 mg/L.

In an embodiment, a dosage of the PMS is 20-200 mg/L.

In an embodiment, the pH of the antibiotic wastewater is adjusted to 10-11 with a 0.1 mol/L sodium hydroxide solution or a 0.1 mol/L hydrochloric acid solution; and during the degradation treatment of the antibiotic wastewater, a pH change of the antibiotic wastewater is detected every 10 min, and the pH of the antibiotic wastewater is maintained at 10-11.

In an embodiment, the antibiotic wastewater is selected from the group consisting of tetracycline wastewater, macrolide wastewater, aminoglycoside wastewater, and a combination thereof.

The above-mentioned method of preparing the FeMnCeO$_x$ biomaterial and the method of treating antibiotic wastewater are utilized. The prepared FeMnCeO$_x$ biomaterial is fed to antibiotic wastewater and is supplemented with PMS. In the system of FeMnCeO$_x$ and PMS, PMS is activated by the FeMnCeO$_x$ to induce the generation of active substances, such as hydroxyl radicals, sulphate salt radicals and single-linear oxygen radicals to undergo a series of physicochemical reactions and free radical chain reactions occur, efficiently degrading antibiotics in the wastewater and achieving the removal of pollutants.

Compared with the prior art, this application has the following beneficial effects.

(1) The FeMnCeO$_x$ biomaterial prepared herein is synthesized by microorganisms rather than chemical methods. Therefore, there is no needs for large consumption of chemicals, and the preparation of the FeMnCeO$_x$ biomaterial can be completed under neutral and environmental-friendly conditions.

(2) The Bio-FeMnCeO$_x$ biomaterial has a large specific surface area, and can induce a wide variety of free radicals with high activity.

(3) The method has the advantages of simple process, short treatment time, convenient operation, low treatment cost, large treatment range and no secondary pollution.

When treating the tetracycline wastewater using the FeMnCeO$_x$ biomaterial, the degradation efficiency of antibiotics is still as high as 86.5% after five times of recycling. It can be seen that the PMS activator of the present disclosure is a new type of catalytic activator with good stability, corrosion resistance and high efficiency, which has good prospects for practical application.

DETAILED DESCRIPTION OF EMBODIMENTS

Figure 1:
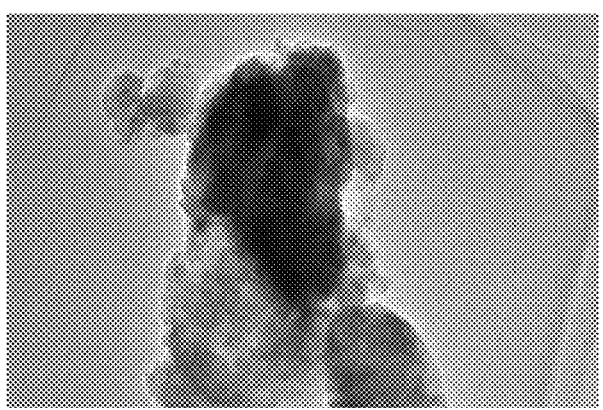
FIG. 1 is a scanning electron microscope (SEM) image of a FeMnCeO$_x$ biomaterial prepared according to an embodiment of the present disclosure.

The technical solutions of the present disclosure will be described clearly and completely in conjunction with the embodiments of the present disclosure. It is obvious that the described herein are only some embodiments of the present disclosure, which are not intended to limit the present disclosure. Based on the embodiments in the present disclosure, all other embodiments obtained by one of ordinary skill in the art without making creative effort shall fall within the scope of the present disclosure.

In a first aspect, this application provides a method of preparing a method of preparing a FeMnCeO$_x$ biomaterial, which includes the following steps.

A KW-2 strain is obtained, where the KW-2 strain is *Pseudomonas* sp. strain KW-2 with a national center for biotechnology information (NCBI) accession number of OM763989.

A culture medium is prepared, where the culture medium includes 0.1 g/L K$_2$HPO$_4$, 0.2 g/L MnSO$_4$·7H$_2$O, 0.2 g/L NaNO$_3$, 0.1 g/L CaCl$_2$), 0.1 g/L NH$_4$Cl, 0.1 g/L (NH$_4$)$_2$CO$_3$, 35 g/L NaCl and 150 mg ferric ammonium citrate; and a pH of the culture medium is 6.5-7.8.

The culture medium is autoclaved, inoculated with the KW-2 strain and cultured for 1-3 days, where the KW-2 strain is 2-10% by volume of the culture medium. Then the culture medium is added with a cerium nitrate solution, cultured for 3-7 days and centrifuged at 4,000-8,000 rpm for 10-20 min to collect a precipitate.

The precipitate is rinsed 5-8 times with deionized water and 0.01 mol/L phosphate buffered saline (PBS) and freeze-dried at −60° C. to obtain the FeMnCeO$_x$ biomaterial.

The PBS buffer is one of the most widely used buffers in biochemistry research, which is mainly composed of Na$_2$HPO$_4$, KH$_2$PO$_4$, NaCl and KCl. The PBS buffer is generally used as a solvent to protect reagents. The PBS buffer has a wide range of pH due to the secondary dissociation of the Na$_2$HPO$_4$ and KH$_2$PO$_4$, while NaCl and KCl mainly serve to increase the ion concentration.

In an embodiment, during preparation of the culture medium, a MnSO$_4$·7H$_2$O is added, and a concentration of divalent manganese ions in the MnSO$_4$·7H$_2$O solution is 20-140 mg/L.

In an embodiment, during preparation of the culture medium, a ferric ammonium citrate solution is added, and a concentration of trivalent iron ions in the ferric ammonium citrate solution is 50-180 mg/L.

In an embodiment, a concentration of cerium ions in the cerium nitrate solution is 5-50 mg/L.

In an embodiment, the autoclaving is performed at 121° C. for 15 min; and the first culturing is performed at a rotation speed of 130 rpm and 25° C.

In a second aspect, this application provides a method for treating antibiotic wastewater, which includes the following steps.

A FeMnCeO$_x$ biomaterial is obtained by using the aforementioned method.

The FeMnCeO$_x$ biomaterial and a permonosulphate (PMS) are added into the antibiotic wastewater. A pH of the antibiotic wastewater is adjusted followed by uniform mixing for degradation treatment of the antibiotic wastewater.

In an embodiment, a dosage of the FeMnCeO$_x$ biomaterial is 10-200 mg/L.

In an embodiment, a dosage of the PMS is 20-200 mg/L.

In an embodiment, the pH of the antibiotic wastewater is adjusted to 10-11 by using a 0.1 mol/L sodium hydroxide solution or a 0.1 mol/L hydrochloric acid solution; and during the degradation treatment of the antibiotic wastewater, a pH change of the antibiotic wastewater is detected every 10 min, and the pH of the antibiotic wastewater is maintained at 10-11.

In an embodiment, the antibiotic wastewater is selected from the group consisting of tetracycline wastewater, macrolide wastewater, aminoglycoside wastewater, and a combination thereof.

Specific examples are listed below for detailed description.

Example 1

Provided herein was a method of preparing a FeMnCeO$_x$ biomaterial.

The manganese oxidizing bacterium used herein was *Pseudomonas* sp. strain KW-2 with a NCBI accession number of OM763989.

The culture medium used herein included 0.1 g/L K$_2$HPO$_4$, 0.2 g/L MnSO$_4$·7H$_2$O, 0.2 g/L NaNO$_3$, 0.1 g/L CaCl$_2$, 0.1 g/L NH$_4$Cl, 0.1 g/L (NH$_4$)$_2$CO$_3$, 35 g/L NaCl, and 150 mg/L (i.e., the concentration of Fe (III)) ferric ammonium citrate solution. The pH of the culture medium was 7.0.

The culture medium was autoclaved at 121° C. for 15 min, inoculated with the KW-2 strain and cultured at 130 rpm and 25° C. for 2 days, where the KW-2 strain was 5% by volume of the culture medium. Then the culture medium is added with a 50 mg/L (i.e., the concentration of Ce) cerium nitrate solution, cultured for 5 days and centrifuged at 6,000 rpm for 15 min to collect a precipitate.

The precipitate was rinsed 6 times with deionized water and 0.01 mol/L PBS buffer (pH=7.0) and freeze-dried at −60° C. to obtain the FeMnCeO$_x$ biomaterial.

Figure 2:
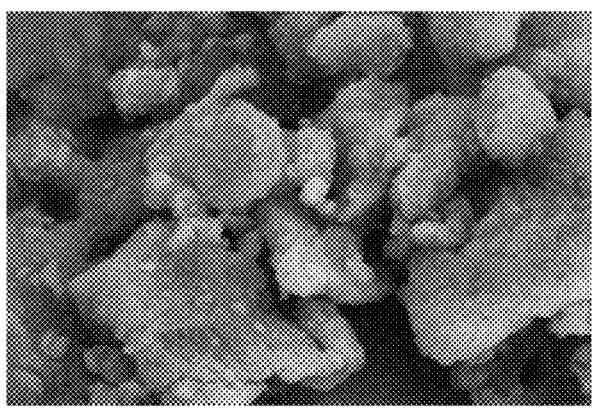
FIG. 2 is a transmission electron microscope (TEM) image of the FeMnCeO$_x$ biomaterial according to an embodiment of the present disclosure.

FIG. 1 and FIG. 2 were a scanning electron microscope (SEM) image and a transmission electron microscope (TEM) image of the FeMnCeO$_x$ biomaterial provided in this example, respectively. From FIGS. 1 and 2, the FeMnCeO$_x$ biomaterial consisted of irregular agglomerates and layered mineral aggregates accompanied by a large number of nanoparticle agglomerates on the surface. The semi-quantitative analysis of the energy dispersive system (EDS) showed that the elemental composition of the FeMnCeO$_x$ mainly included O, C, Fe, Mn, and Ce, with the contents of 26.6%, 20.6%, 12.7%, 8.5% and 7.2%, respectively.

Example 2

Provided herein was a method of preparing a FeMnCeO$_x$ biomaterial.

The manganese oxidizing bacterium used herein was *Pseudomonas* sp. strain KW-2 with a NCBI accession number of OM763989.

The culture medium used herein included 0.1 g/L K$_2$HPO$_4$, 0.2 g/L MnSO$_4$·7H$_2$O, 0.2 g/L NaNO$_3$, 0.1 g/L CaCl$_2$, 0.1 g/L NH$_4$Cl, 0.1 g/L (NH$_4$)$_2$CO$_3$, 35 g/L NaCl, and 120 mg/L (i.e., the concentration of Fe (III)) ferric ammonium citrate solution. The pH of the culture medium was 7.0.

The culture medium was autoclaved at 121° C. for 15 min, inoculated with the KW-2 strain and cultured at 150 rpm and 25° C. for 3 days, where the KW-2 strain was 4% by volume of the culture medium. Then the culture medium is added with a 25 mg/L (i.e., the concentration of Ce) cerium nitrate solution, cultured for 7 days and centrifuged at 8,000 rpm for 20 min to collect a precipitate.

The precipitate was rinsed 6 times with deionized water and 0.01 mol/L PBS buffer (pH=7.0) and freeze-dried at −60° C. to obtain the FeMnCeO$_x$ biomaterial.

Figure 3:
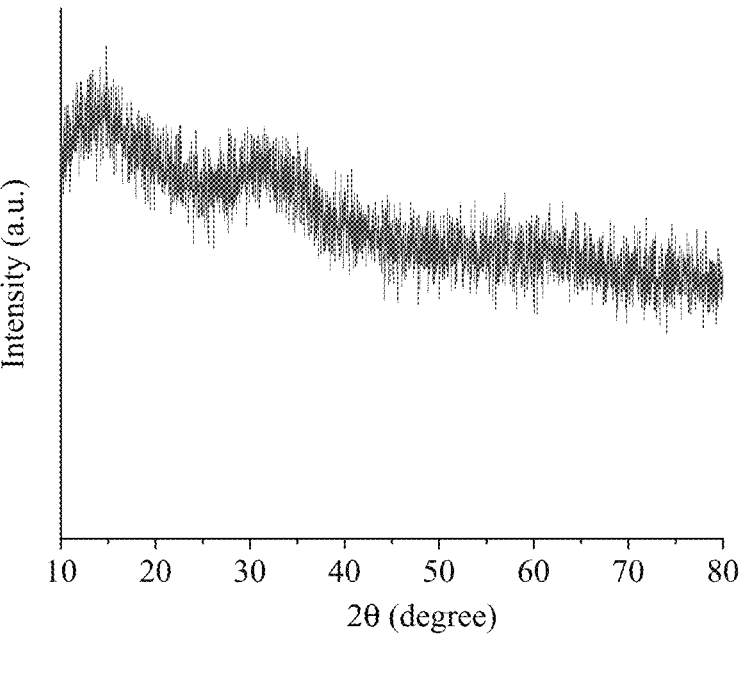
FIG. 3 is an X-ray diffraction (XRD) pattern of the FeMnCeO$_x$ biomaterial according to an embodiment of the present disclosure.

FIG. 3 was a XRD pattern of the FeMnCeO$_x$ biomaterial prepared herein. As could be seen from FIG. 3, two diffraction peaks with weak intensity appeared at 2θ of 15° and 30°, and were broad and blunt, indicating that the biosynthesized FeMnCeO$_x$ was mainly weakly crystalline or amorphous. Therefore, the FeMnCeO$_x$ biomaterial was a weakly crystalline or amorphous layered polymeric manganese oxide.

Example 3

Provided herein was a method of preparing a FeMnCeO$_x$ biomaterial.

The manganese oxidizing bacterium used herein was *Pseudomonas* sp. strain KW-2 with a NCBI accession number of OM763989.

The culture medium used herein included 0.1 g/L K$_2$HPO$_4$, 0.2 g/L MnSO$_4$·7H$_2$O, 0.2 g/L NaNO$_3$, 0.1 g/L CaCl$_2$), 0.1 g/L NH$_4$Cl, 0.1 g/L (NH$_4$)$_2$CO$_3$, 35 g/L NaCl, and 150 mg/L (i.e., the concentration of Fe (III)) ferric ammonium citrate solution. The pH of the culture medium was 7.0.

The culture medium was autoclaved at 121° C. for 15 min, inoculated with the KW-2 strain and cultured at 150 rpm and 30° C. for 2 days, where the KW-2 strain was 4% by volume of the culture medium. Then the culture medium is added with a 100 mg/L (i.e., the concentration of Ce) cerium nitrate solution, cultured for 7 days and centrifuged at 8,000 rpm for 20 min to collect a precipitate.

The precipitate was rinsed 6 times with deionized water and 0.01 mol/L PBS buffer (pH=7.0) and freeze-dried at −60° C. to obtain the FeMnCeO$_x$ biomaterial.

Example 4

Provided herein was a method for treating antibiotic wastewater, where the FeMnCeO$_x$ biomaterial prepared in Example 1 was used to activate PMS for the oxidative degradation of tetracycline, which included the following steps.

200 mL of tetracycline wastewater with an initial concentration of 20 mg/L was taken, stirred, and sequentially added with PMS and the FeMnCeO$_x$ biomaterial for reaction, where a concentration of PMS was 0.15 g/L, and an addition amount of the FeMnCeO$_x$ biomaterial was 150 mg/L. After the reaction was completed, the degradation of the tetracycline wastewater was completed. During the reaction, 4 mL of reaction solution was extracted every 10 min and centrifuged at 8000 rpm for 10 min. After that, the supernatant was detected by a liquid chromatograph instrument. In addition, the pH changes were monitored periodically to maintain the pH of the reaction solution at 11.

Table 1 showed effects of reaction times on degradation effects of the FeMnCeO$_x$/PMS system on tetracycline in the wastewater. As shown in Table 1, the PMS activated by the FeMnCeO$_x$ had good catalytic activity for the degradation of tetracycline. The degradation of tetracycline was 90.7% at 10 min and increased to 93.8% at 60 min, which indicated that the FeMnCeO$_x$ could effectively activate PMS to induce the generation of free radicals, such as sulfate radical and hydroxyl radical, thus accelerating the oxidative degradation of tetracycline.

TABLE 1

Effects of reaction times on degradation effects of the FeMnCeO$_x$/PMS system on tetracycline in the wastewater

| Reaction time (min) | 10 | 20 | 30 | 40 | 50 | 60 |
|---|---|---|---|---|---|---|
| Degradation efficiency (%) | 90.7 | 91.6 | 92.3 | 92.9 | 93.1 | 93.8 |

Example 5

Provided herein was a method for treating antibiotic wastewater, where the FeMnCeO$_x$ biomaterial prepared in Example 2 was used to activate PMS for the oxidative degradation of tetracycline, which included the following steps.

200 mL of tetracycline wastewater with an initial concentration of 20 mg/L was taken, stirred, and sequentially added with PMS and the FeMnCeO$_x$ biomaterial for reaction, where a concentration of PMS was 0.2 g/L, and a dosage of the FeMnCeO$_x$ biomaterial was 100 mg/L. After the reaction was completed, the degradation of the tetracycline wastewater was completed. In addition, the pH changes and the antibiotic concentration were monitored periodically, and the pH of the reaction solution was maintained at 10.5.

Table 2 showed effects of culture time on degradation efficiency of the FeMnCeO$_x$/PMS system for tetracycline in the wastewater. As shown in Table 2, the PMS activated by the FeMnCeO$_x$ biomaterials obtained with different culture time had good catalytic activity for the degradation of tetracycline. The degradation efficiency of tetracycline was 85.6% at a culture time of 3 days and increased to 88.6% at a culture time of 9 days. However, the degradation efficiency of tetracycline was only 82.2% when the culture time was extended to 11 days.

TABLE 2

Effects of culture time of the FeMnCeO$_x$ on degradation efficiency of the FeMnCeO$_x$/PMS system for tetracycline in the wastewater

| Culture time (d) | 3 | 5 | 7 | 9 | 11 |
|---|---|---|---|---|---|
| Degradation efficiency (%) | 85.6 | 83.1 | 88.0 | 88.6 | 82.2 |

Example 6

Provided herein was a method for treating antibiotic wastewater, where the FeMnCeO$_x$ biomaterial prepared in Example 3 was used to activate PMS for the oxidative degradation of tetracycline, which included the following steps.

200 mL of tetracycline wastewater with an initial concentration of 20 mg/L was taken, stirred, and sequentially added with PMS and the FeMnCeO$_x$ biomaterial for reaction, where a concentration of PMS was 0.1 g/L, and an addition amount of the FeMnCeOx biomaterial was 50 mg/L. After the reaction was completed, the degradation of the tetracycline wastewater was completed. In addition, the antibiotic concentration was monitored periodically.

Table 3 showed effects of pH on tetracycline degradation efficiency by FeMnCeO$_x$-activated PMS. As shown in Table 3, different pH values had effects on degradation efficiency for tetracycline by FeMnCeO$_x$-activated PMS. The degradation efficiency of tetracycline was 71.7% at pH 7, whereas 84.9% at pH 9 and 91.6% at pH 11. It indicated that the catalytic degradation of tetracycline was more efficient under strong alkaline (pH=11) conditions, because OH$^-$ could promote the decomposition of HSO$_5^-$ and accelerated the generation of SO$_4^{\cdot-}$ radicals under alkaline conditions. Moreover, the strong alkaline conditions also inhibited the solubilization of metals, i.e., Ce, Fe and Mn.

TABLE 3

Effects of pH on degradation efficiency for tetracycline by FeMnCeO$_x$-activated PMS

| pH | 3 | 5 | 7 | 9 | 11 |
|---|---|---|---|---|---|
| Degradation efficiency (%) | 89.6 | 88.3 | 71.7 | 84.9 | 91.6 |

Example 7

Provided herein was a method for treating antibiotic wastewater, where the FeMnCeO$_x$ biomaterial prepared in Example 1 was used to activate PMS for the oxidative degradation of tetracycline, which included the following steps.

200 mL of tetracycline wastewater with an initial concentration of 20 mg/L was taken, stirred, and sequentially added with PMS and the FeMnCeOx biomaterial for reaction, where a concentration of PMS was 0.02-0.2 g/L, and an addition amount of the FeMnCeO$_x$ biomaterial was 100 mg/L. After the reaction was completed, the degradation of the tetracycline wastewater was completed. In addition, the pH changes and the antibiotic concentration were monitored periodically, and the pH of the reaction solution was maintained at 11.

Table 4 showed effects of PMS concentration on degradation efficiency for tetracycline by FeMnCeO$_x$-activated PMS. As shown in Table 4, PMS concentrations had effects on the degradation efficiency of tetracycline. The degradation efficiency of tetracycline was only 62.7% at a PMS concentration of 0.02 g/L, whereas the degradation efficiency of tetracycline increased to 91.8% when the PMS concentration was increased to 0.2 g/L. The results showed that PMS could effectively activate the FeMnCeO$_x$ biomaterial to produce more ·OH and SO$_4^{\cdot-}$ radicals, thus improving the degradation efficiency of tetracycline.

TABLE 4

| Effects of PMS concentration on degradation efficiency for tetracycline by FeMnCeO$_x$-activated PMS | | | | | |
| --- | --- | --- | --- | --- | --- |
| PMS concentration (g/L) | 0.02 | 0.05 | 0.1 | 0.15 | 0.2 |
| Degradation efficiency (%) | 62.7 | 74.2 | 78.8 | 86.9 | 91.8 |

Example 8

Provided herein was a method for treating antibiotic wastewater, where the FeMnCeO$_x$ biomaterial prepared in Example 3 was used to activate PMS for the oxidative degradation of tetracycline, which included the following steps.

200 mL of tetracycline wastewater with an initial concentration of 20 mg/L was taken, stirred, and sequentially added with PMS and the FeMnCeO$_x$ biomaterial for reaction, where a concentration of PMS was 0.2 g/L, and an addition amount of the FeMnCeOx biomaterial was 10-200 mg/L. After the reaction was completed, the degradation of the tetracycline wastewater was completed. In addition, the pH changes and the antibiotic concentration were monitored periodically, and the pH of the reaction solution was maintained at 11.

Table 5 showed dosage effects of the FeMnCeO$_x$ biomaterial on degradation efficiency for tetracycline by FeMn-CeO$_x$-activated PMS. As shown in Table 5, addition amounts of the FeMnCeO$_x$ biomaterial had effects on degradation efficiency for tetracycline. The degradation efficiency of tetracycline was only 71.8% when the dosage of the FeMnCeO$_x$ biomaterial was 10 mg/L, and the degradation efficiency of tetracycline was 89.7% when the dosage of the FeMnCeO$_x$ biomaterial was increased to 20 mg/L. However, the degradation efficiency of tetracycline did not continue to increase when the dosage of the FeMnCeO$_x$ biomaterial was further increased. On one hand, when the dosage of the FeMnCeO$_x$ biomaterial reached a certain level, the saturation of the active sites was already saturated. On the other hand, when the dosage of the FeMnCeO$_x$ biomaterial was high, the FeMnCeO$_x$ biomaterial was easily aggregated to form flocs with large particles, which resulted in poor dispersion and a significant decrease in the specific surface area, leading to a decrease in the degradation efficiency of tetracycline.

TABLE 5

| Dosage effects of the FeMnCeO$_x$ biomaterial on degradation efficiency for tetracycline by FeMnCeO$_x$-activated PMS | | | | | |
| --- | --- | --- | --- | --- | --- |
| Dosage (mg/L) | 10 | 20 | 50 | 100 | 200 |
| Degradation efficiency (%) | 71.8 | 89.7 | 88.8 | 86.8 | 84.0 |

Example 9

Figure 4:
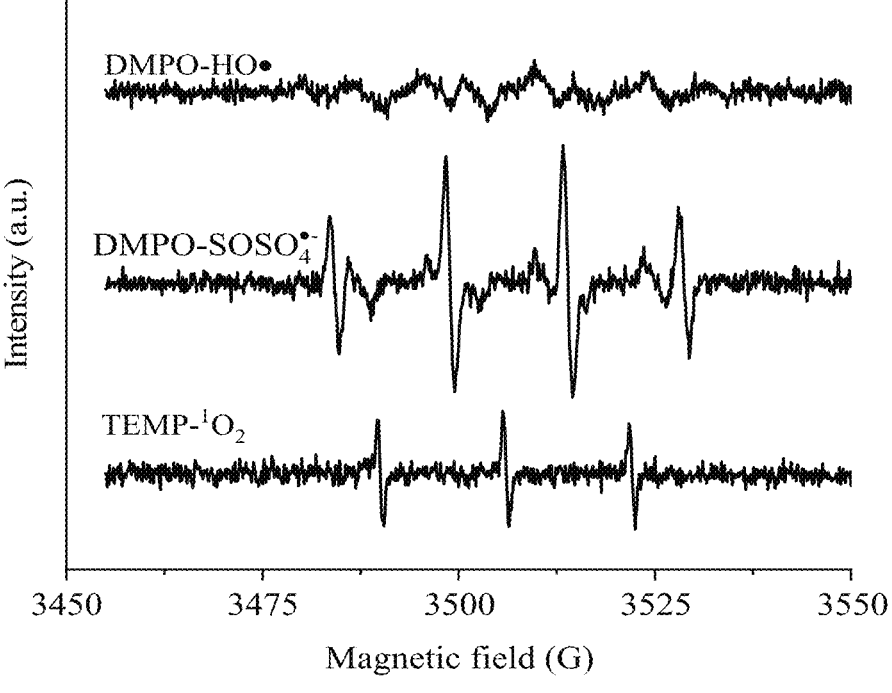
FIG. 4 an electron paramagnetic resonance (EPR) spectrum of a FeMnCeO$_x$/permonosulphate (PMS) system according to an embodiment of the present disclosure.

To further identify the main radical species of the FeMn-CeO$_x$/PMS reaction system, the signal characteristics of each reactive oxygen species were analyzed by electron paramagnetic resonance (EPR) using 2,4,5,6-tetraaminopyridine (TEMP) and 5,5-dimethyl-1-pyrroline N-oxide (DMPO) as trapping agents. FIG. 4 was a EPR test spectrum of the FeMnCeO$_x$/PMS system, which showed obvious characteristic peaks of HO·, SO$_4$·$^-$ and $^1$O$_2$ radical signals in all the reaction systems. Notably, the intensities of SO$_4$·$^-$ and $^1$O$_2$ radical signals were significantly higher than that of HO·, indicating that the SO$_4$·$^-$ and $^1$O$_2$ radicals exhibited a crucial role in the tetracycline degradation process.

Figure 5:
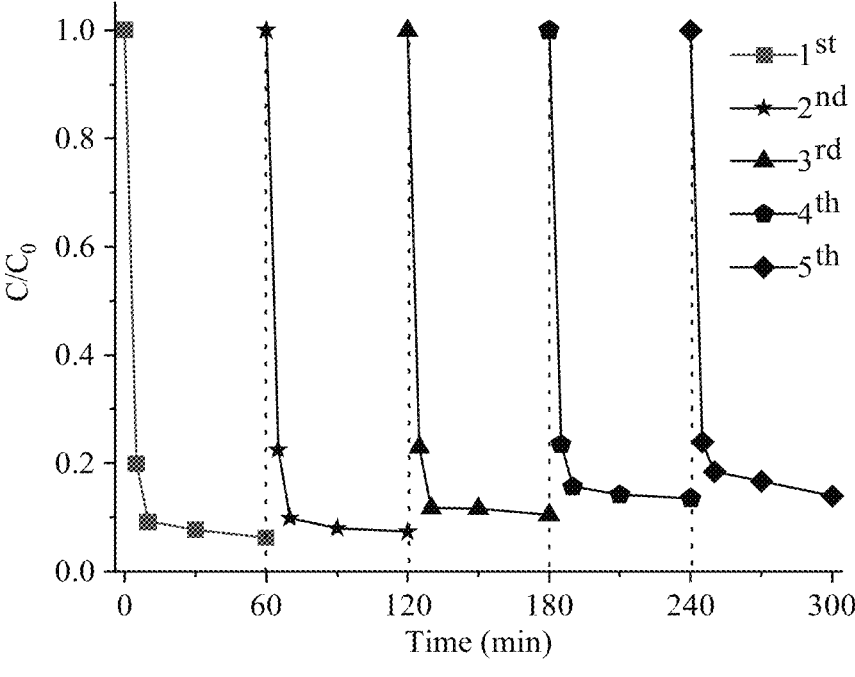
FIG. 5 shows cycling stability of the FeMnCeO$_x$ biomaterial according to an embodiment of the present disclosure in the degradation of tetracycline.
Figure 6:
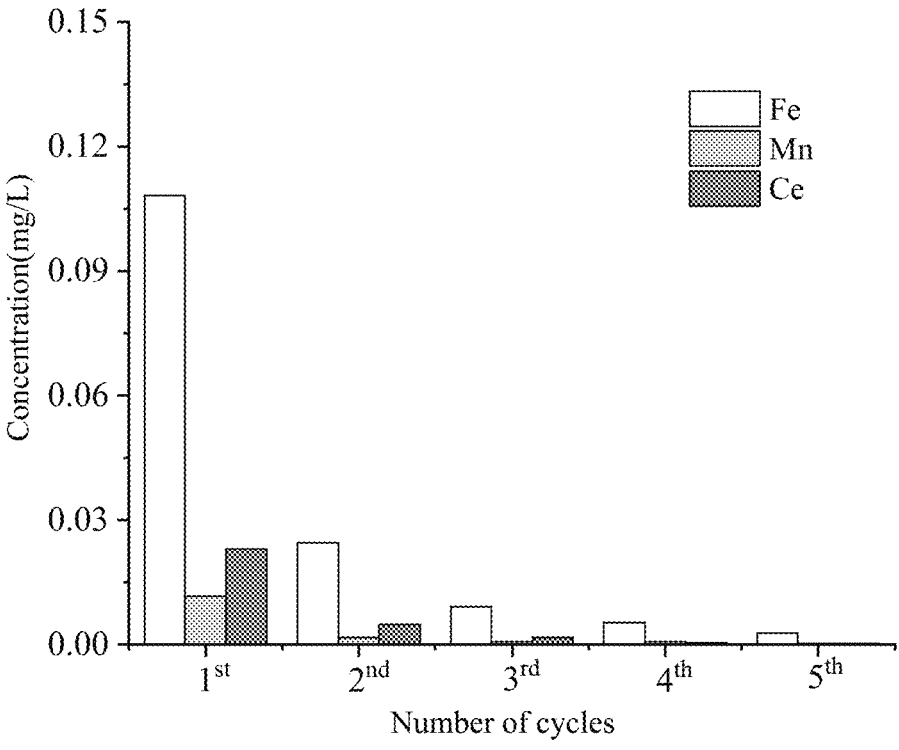
FIG. 6 shows dissolution of metal ions from the FeMnCeO$_x$ biomaterial according to an embodiment of the present disclosure during the cycling tetracycline degradation.

To investigate the chemical stability of FeMnCeO$_x$ biomaterial, the FeMnCeO$_x$ biomaterial that activated PMS was reused under the same conditions, and the degradation efficiency of tetracycline and the solubilization of metal ions were analyzed for different number of cycles. FIG. 5 showed the cyclic stability of tetracycline degradation by the FeMn-CeOx biomaterial. FIG. 6 shows dissolution of metal ions during a cycling process of tetracycline degradation using the FeMnCeO$_x$ biomaterial As shown in FIG. 5, the degradation efficiency of tetracycline decreased from 93.75% to 86.48% after five cycles. The decrease in the degradation efficiency of biomaterials might be caused by the residual tetracycline degradation products on the surface of biomaterials and the leaching of metal ions. In addition, it could be seen from FIG. 6 that during the recycling process of the FeMnCeO$_x$ biomaterial, the release of Fe$^{2+}$, Mn$^{2+}$, and Ce$^{3+}$ existed, but the release of the three ions decreased dramatically with the increase of the number of cycles. Among them, after 5 cycles, the Fe$^{2+}$ concentration decreased from 0.108 mg/L in the 1$^{st}$ cycle to 0.003 mg/L. Overall, the degradation efficiency of tetracycline was still higher than 85% after 5 cycles of reuse, indicating that the biosynthesized FeMnCeO$_x$ material had good cycling stability and reusability.

As can be seen from the above embodiments, efficient treatment of antibiotic wastewater can be achieved by the method described in the present invention. In conclusion, the method provided herein has the advantages of simple process, short restoration time, convenient operation, low treatment cost, large treatment range and no secondary pollution.

The above-mentioned method of preparing the FeMn-CeO$_x$ biomaterial and the method of treating antibiotic wastewater are utilized. The prepared FeMnCeO$_x$ biomaterial is fed to antibiotic wastewater and is supplemented with PMS. In the system of FeMnCeO$_x$ and PMS, PMS is activated by the FeMnCeO$_x$ to induce the generation of active substances, such as hydroxyl radicals, sulphate salt radicals and single-linear oxygen radicals to undergo a series of physicochemical reactions and free radical chain reactions occur, efficiently degrading antibiotics in the wastewater and achieving the removal of pollutants.

The method provided in this application at least has the following beneficial effects.

(1) The FeMnCeO$_x$ biomaterial prepared herein is synthesized by microorganisms rather than chemical methods. Therefore, there is no needs for large consumption of chemicals, and the preparation of the FeMnCeO$_x$ biomaterial can be completed under neutral and environmental-friendly conditions.

(2) The Bio-FeMnCeOx biomaterial has a large specific surface area, and can induce a wide variety of free radicals with high activity.

(3) The method has the advantages of simple process, short treatment time, convenient operation, low treatment cost, large treatment range and no secondary pollution.

After recycled five times, the FeMnCeO$_x$ biomaterial still exhibited a desirable degradation efficiency (86.5%) to antibiotics in the treatment of the tetracycline wastewater. It can be concluded that the PMS activator of the present disclosure is a novel catalytic activator with excellent stability, desirable corrosion resistance and high efficiency, and thus has brilliant application prospects.

In the above embodiments, the description of each embodiment has its own focus, and the part that is not detailed in a certain embodiment can be seen in the relevant description of other embodiments.

Described above are detail description of the embodiments of the present application, and principles and implementations of the present application are illustrated with reference to specific examples. The descriptions of the above embodiments are merely used to facilitate the understanding of the technical solutions and the core ideas of the present application. It should be understood by one of ordinary skill in the art that it is still possible to make modifications or equivalent substitutions to the technical solutions recited in the foregoing embodiments, and those modifications or substitutions made without departing from the spirit of the disclosure shall fall within the scope of the disclosure defined by the appended claims.

What is claimed is:

1. A method of preparing a FeMnCeO$_x$ biomaterial, comprising:

obtaining a KW-2 strain, wherein the KW-2 strain is *Pseudomonas* sp. strain KW-2 with a national center for biotechnology information (NCBI) accession number of OM763989;

preparing a culture medium, wherein the culture medium comprises 0.1 g/L K$_2$HPO$_4$, 0.2 g/L MnSO$_4$·7H$_2$O, 0.2 g/L NaNO$_3$, 0.1 g/L CaCl$_2$, 0.1 g/L NH$_4$Cl, 0.1 g/L (NH$_4$)$_2$CO$_3$, 35 g/L NaCl and 150 mg/L ferric ammonium citrate; and a pH of the culture medium is 6.5-7.8;

autoclaving the culture medium; inoculating the KW-2 strain into the culture medium followed by a first culture for 1-3 days, wherein the KW-2 strain is 2-10% by volume of the culture medium; and adding a cerium nitrate solution into the culture medium followed by a second culture for 3-7 days and centrifugation at 4,000-8,000 rpm for 10-20 min to collect a precipitate; and rinsing the first precipitate 5-8 times with deionized water and a 0.01 mol/L phosphate buffered saline (PBS) followed by freeze-drying at −60° C. to obtain the FeMnCeO$_x$ biomaterial.

2. The method of claim 1, wherein during preparation of the culture medium, a MnSO$_4$·7H$_2$O solution is added, and a concentration of divalent manganese ions in the MnSO$_4$·7H$_2$O solution is 20-140 mg/L.

3. The method of claim 1, wherein during preparation of the culture medium, a ferric ammonium citrate solution is added, and a concentration of ferric ions in the ferric ammonium citrate solution is 50-180 mg/L.

4. The method of claim 1, wherein a concentration of cerium ions in the cerium nitrate solution is 5-50 mg/L.

5. The method of claim 1, wherein the culture medium is autoclaved at 121° C. for 15 min; and the first culture is performed at a rotation speed of 130 rpm and 25° C.

6. A method for treating an antibiotic wastewater, comprising:

preparing a FeMnCeO$_x$ biomaterial using the method of claim 1; and adding the FeMnCeO$_x$ biomaterial and a permonosulphate (PMS) into the antibiotic wastewater; and adjusting pH of the antibiotic wastewater followed by uniform mixing for degradation treatment of the antibiotic wastewater.

7. The method of claim 6, wherein a dosage of the FeMnCeO$_x$ biomaterial is 10-200 mg/L.

8. The method of claim 6, wherein a dosage of the PMS is 20-200 mg/L.

9. The method of claim 6, wherein the pH of the antibiotic wastewater is adjusted to 10-11 with a 0.1 mol/L sodium hydroxide solution or a 0.1 mol/L hydrochloric acid solution; and during the degradation treatment of the antibiotic wastewater, a pH change of the antibiotic wastewater is detected every 10 min, and the pH of the antibiotic wastewater is maintained at 10-11.

10. The method of claim 6, wherein the antibiotic wastewater is selected from the group consisting of tetracycline wastewater, macrolide wastewater, aminoglycoside wastewater, and a combination thereof.

* * * * *